United States Patent [19]

Slough et al.

[11] 4,409,553
[45] Oct. 11, 1983

[54] PARAFFIN MONITOR

[75] Inventors: Carlton M. Slough, Spring; Edwin L. Colling, Jr., Sugarland, both of Tex.

[73] Assignee: Texaco Inc., White Plains, N.Y.

[21] Appl. No.: 371,359

[22] Filed: Apr. 23, 1982

Related U.S. Application Data

[63] Continuation of Ser. No. 194,696, Oct. 6, 1980, abandoned.

[51] Int. Cl.³ ............... G01N 27/00; G01N 33/28
[52] U.S. Cl. ................. 324/445; 324/204; 422/68; 422/119; 436/141; 436/149
[58] Field of Search .......... 324/236, 204, 442, 239, 324/445, 446, 439, 65 CR, 61 QL, 65 R; 422/68, 119; 23/230 HC, 230 M; 331/65; 436/141, 149

[56] References Cited

U.S. PATENT DOCUMENTS

| | | | |
|---|---|---|---|
| 2,542,057 | 2/1951 | Relis | 324/445 |
| 2,836,792 | 5/1958 | Weber | 324/65 R |
| 3,256,483 | 6/1966 | Broadbent | 324/65 R |
| 3,315,155 | 4/1967 | Colani | 324/239 |
| 3,724,474 | 4/1973 | De Vale | 324/65 R |
| 3,757,210 | 9/1973 | Hansen et al. | 324/65 CR |
| 3,879,657 | 4/1975 | Nystuen et al. | 324/442 |
| 4,039,934 | 8/1977 | Ostashko et al. | 324/442 |
| 4,116,045 | 9/1978 | Potter | 23/230 HC |

Primary Examiner—Kenneth M. Schor
Attorney, Agent, or Firm—Carl G. Ries; Robert A. Kulason; Ronald G. Gillespie

[57] ABSTRACT

A paraffin monitor includes a pulse source periodically providing pulses. Apparatus, adapted to be immersed in a medium having paraffin, provides an output signal in response to each pulse in accordance with a paraffin film grown on said apparatus while the apparatus is immersed in the medium.

6 Claims, 3 Drawing Figures

OUTPUT SIGNAL

DECAY TIME NO PARAFFIN FILM

OUTPUT SIGNAL

DECAY TIME WITH PARAFFIN FILM

PARAFFIN MONITOR

CROSS REFERENCE TO RELATED APPLICATIONS

This application is a continuation as to all subject matter common to U.S. application Ser. No. 194,696, now abandoned and filed Oct. 6, 1980 by Carlton M. Slough and Edwin L. Colling, Jr. and assigned to Texaco Inc., assignee of the present invention, and a continuation-in-part for additional subject matter.

BACKGROUND OF THE INVENTION

Field of the Invention

The present invention relates to monitors in general and, more particularly, to monitors for monitoring paraffin and the effectiveness of paraffin inhibitors and dispersants.

SUMMARY OF THE INVENTION

A paraffin monitor includes a source which periodically provides pulses. A circuit adapted to be immersed in a medium having paraffin is connected to the source and energized by the source so that when immersed in the medium the output signal from the circuit will be representative of the paraffin growth affecting the circuit.

The objects and advantages of the invention will appear more fully hereinafter from a consideration of the detailed description which follows, taken together with the accompanying drawings wherein one embodiment of the invention is illustrated by way of example. It is to be expressly understood, however, that the drawings are for illustration purposes only and are not to be construed as defining the limits of the invention.

DESCRIPTION OF THE INVENTION

Figure 1:
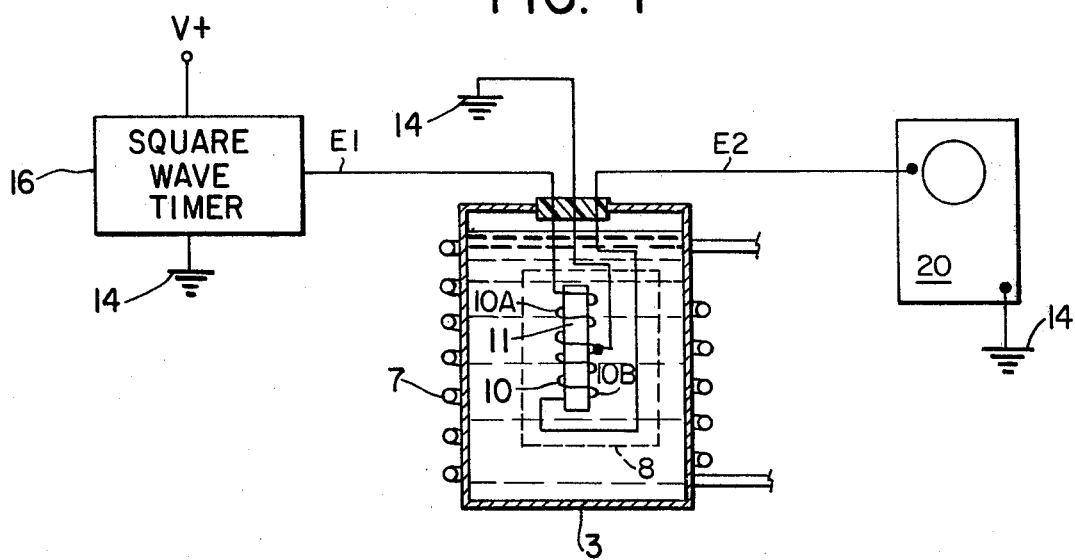
FIG. 1 is a partial block diagram and a partial schematic of a paraffin monitor constructed in accordance with the present invention.

Referring to FIG. 1, a container 3 heated by a heater wire 7 from a heater source, not shown, contains a medium having paraffin. For the purpose of the present invention, the word "medium" will be used to denote a liquid containing some crude oil having paraffin or a liquid that is substantially all, if not 100 percent, crude oil or waxy oil which is usually present in refineries. A magnetostriction oscillator 8 which includes a wire 10 wrapped around a metal rod 11 in which the wire has a center tap connected to ground 14 so as to form two coils 10A and 10B. One end of the coil 10A is connected to a square wave timer 16 which may be of the type manufactured by Signetics as their model number NE555 which is also connected to ground 14. One end of coil 10B is connected to an oscilloscope 20 which in turn is connected to ground 14.

Although magnetostriction oscillators are old and well known in the art they have not been applied as is being done with the present invention. An explanation of how these oscillators operate may be in order. Magnetostriction in metals is somewhat analogous to the piezoelectric affect in quartz crystal. There is an expansion or contraction of magnetic material as a result of magnetization and conversely a change of magnetic permeability as a result of mechanical stress. Metallic rods exhibit resonance characteristics just as crystals do and the frequency of resonance depends on the material and the physical size of the rod. If a rod of magnetostrictive material is placed in a suitable alternating field the rod will vibrate longitudinally at a frequency which is twice that of the exciting field. Under this condition the exact center of the rod is a nodal point.

One end of the rod 11 may be excited with a coil wrapped around that end of the rod and a second coil wrapped around the other end may be used as a pick-up coil. As shown in FIG. 1, coil 10A is an excitation coil, while coil 10B is being used as a pick-up coil. The resonant frequency is given by $f = v/2L$ where f is frequency, v is velocity of sound in rod 11 and L is the length of rod 11. With magnetostriction oscillator 8 submerged in a medium the excitation coil 10A is pulsed causing rod 11 to vibrate at its resonant frequency and to exhibit characteristic Q (efficiency), damping and decay behavior.

Deposition of paraffin from the medium on rod 11 changes the Q, damping and decay parameters. These changes are detected and analyzed using oscilloscope 20.

Figure 2:
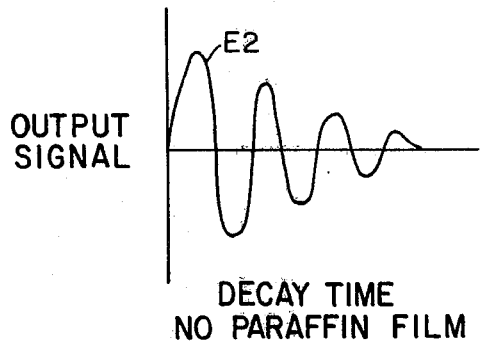
FIGS. 2 and 3 are diagrams of voltage E2 wave forms occurring during the operation of the monitor shown in FIG. 1.
Figure 3:
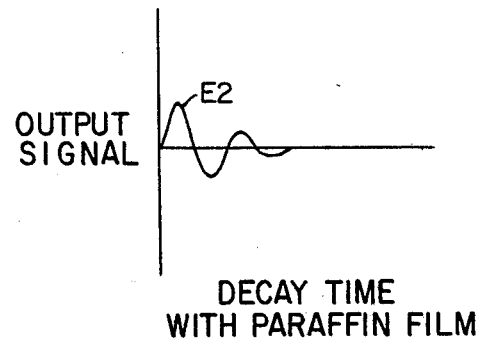

In operation, timer 16 provides a square wave pulse E1 to oscillator 8, causing oscillator 8 to provide a decaying oscillating signal E2, as shown in FIG. 2. Over a period of time, the paraffin in the medium builds-up on rod 11 and affects the Q, damping and decay behavior of oscillator 8 to the extent that when a pulse E1 from timer 16 has been applied to the oscillator, the frequency and decay time of signal E2 changes as shown in FIG. 3, which may be viewed on oscilloscope 20.

When monitoring a paraffin inhibitor or dispersant, the rate of growth of the paraffin film on magnetostriction oscillator 8 is representative of the effectiveness of the paraffin inhibitor or dispersant.

The present invention hereinbefore described is a monitor which monitors the rate of growth of paraffin or the effectiveness of paraffin inhibitors and dispersants. A square wave pulse is applied to a magnetostriction oscillator which, in turn, provides an oscillating signal decaying to zero after termination of the pulse and that over a period of time, as the paraffin affects the operation of the oscillator, the decay time and the frequency of the oscillating signal will change.

What is claimed is:

1. A paraffin monitor which comprises:
   pulse means connected to ground, the pulse means being means for periodically providing electrical pulses to a signal means;
   signal means connected to the pulse means and to ground and immersed in a medium having paraffin, the signal means being means for providing an oscillating decaying signal in response to each pulse from the pulse means, with the frequency and decay time of the oscillating decaying signal decreasing in accordance with the build-up of paraffin on the signal means; and
   indicating means connected to the signal means and to ground, the indicating means being means for providing an indication of the paraffin build-up in accordance with the signal from the signal means.

2. A monitor as described in claim 1 in which said signal means is a magnetostriction oscillator.

3. A monitor as described in claim 2 in which said magnetostriction oscillator includes a metallic rod,
an excitation coil spatially arranged in a predetermined manner with said rod and having one end connected to said pulse means, and another end connected to ground and
a pick-up coil spatially arranged in a predetermined manner with said rod and said excitation coil and having one end connected to said indicating means and another end commonly connected to the ground connected end of said excitation coil, to said pulse means and to said indicating means so that pulses from said pulse means are provided to said excitation coil and said pick-coil provides each oscillating decaying signal to said indicating means.

4. A monitor as described in claim 3 in which the frequency and decay time of the oscillating decaying signal changes in accordance with the growth of paraffin on said rod of said magnetostriction oscillator.

5. A monitor as described in claim 4 in which the indicating means is an oscilloscope.

6. A monitor as described in claim 5 further comprising means for containing and maintaining the medium at a predetermined temperature.

* * * * *